United States Patent
Mindel et al.

(10) Patent No.: US 12,266,142 B2
(45) Date of Patent: Apr. 1, 2025

(54) MONITORING LIVESTOCK IN AN AGRICULTURAL PEN

(71) Applicant: FARMSEE LTD., Hod Hasharon (IL)

(72) Inventors: Anatoly Mindel, Ganey Tikva (IL); Yossi Cohen, Netanya (IL)

(73) Assignee: FARMSEE LTD., Hod Hasharon (IL)

(*) Notice: Subject to any disclaimer, the term of this patent is extended or adjusted under 35 U.S.C. 154(b) by 1071 days.

(21) Appl. No.: 17/256,153

(22) PCT Filed: Jun. 25, 2019

(86) PCT No.: PCT/IL2019/050706
§ 371 (c)(1),
(2) Date: Dec. 24, 2020

(87) PCT Pub. No.: WO2020/003310
PCT Pub. Date: Jan. 2, 2020

(65) Prior Publication Data
US 2021/0153479 A1    May 27, 2021

Related U.S. Application Data

(60) Provisional application No. 62/827,203, filed on Apr. 1, 2019, provisional application No. 62/689,251, filed on Jun. 25, 2018.

(51) Int. Cl.
*G06V 10/22* (2022.01)
*A01K 11/00* (2006.01)
(Continued)

(52) U.S. Cl.
CPC ............ *G06V 10/22* (2022.01); *A01K 11/006* (2013.01); *A01K 29/005* (2013.01); *G06T 7/11* (2017.01);
(Continued)

(58) Field of Classification Search
CPC ..... G06T 7/10; G06T 7/11; G06T 7/12; G06T 2207/20081; G06T 2207/20084;
(Continued)

(56) References Cited

U.S. PATENT DOCUMENTS 9,084,411 B1   7/2015   McGlone et al.
2012/0275659 A1   11/2012   Gomas et al.
(Continued)

FOREIGN PATENT DOCUMENTS

WO   WO-2019044001 A1 *   3/2019   ............. A01K 67/00

OTHER PUBLICATIONS

Wang, Jianyu, and Alan Yuille. "Semantic part segmentation using compositional model combining shape and appearance." 2015 IEEE Conference on Computer Vision and Pattern Recognition (CVPR). IEEE, 2015. (Year: 2015).*

(Continued)

*Primary Examiner* — Geoffrey E Summers
(74) *Attorney, Agent, or Firm* — The Roy Gross Law Firm, LLC; Roy Gross

(57) ABSTRACT

A method comprising: receiving an image of a scene comprising one or more animals; defining region boundaries for each of said one or more animals; evaluating a suitability of each of said region boundaries for further processing, based, at least in part, on a predetermined set of parameters; and determining at least one of: (i) a physical state of at least some of said one or more animals, based, at least in part, on said further processing, and (ii) an identity of at least some of said one or more animals.

15 Claims, 12 Drawing Sheets

(51) Int. Cl.
| | |
|---|---|
| *A01K 29/00* | (2006.01) |
| *G06T 7/11* | (2017.01) |
| *G06V 10/26* | (2022.01) |
| *G06V 10/56* | (2022.01) |
| *G06V 10/82* | (2022.01) |
| *G06V 20/52* | (2022.01) |
| *G06V 40/10* | (2022.01) |
| *G16B 40/00* | (2019.01) |

(52) U.S. Cl.
CPC .............. *G06V 10/26* (2022.01); *G06V 10/56* (2022.01); *G06V 10/82* (2022.01); *G06V 20/52* (2022.01); *G06V 40/10* (2022.01); *G06V 40/103* (2022.01); *G16B 40/00* (2019.02); *G06T 2207/20081* (2013.01)

(58) Field of Classification Search
CPC .... G06T 7/0012; G06V 10/26; G06V 10/267; G06V 10/273; G06V 10/70; G06V 10/764; G06V 10/82; G06V 40/10; G06V 40/103; G06V 10/22; G06V 10/56; G06V 20/52; G06N 3/02–0985; G06N 20/00; G06N 20/20; A01K 11/006; A01K 29/005; G16B 40/00; G01G 17/08
See application file for complete search history.

(56) References Cited

U.S. PATENT DOCUMENTS

| | | | |
|---|---|---|---|
| 2016/0012278 A1* | 1/2016 | Banhazi ................ | G06V 10/44 382/110 |
| 2017/0124727 A1 | 5/2017 | Amat Roldan et al. | |
| 2020/0214266 A1* | 7/2020 | Fujiyama ............... | A01K 11/00 |

OTHER PUBLICATIONS

Andrew, William, Colin Greatwood, and Tilo Burghardt. "Visual Localisation and Individual Identification of Holstein Friesian Cattle via Deep Learning." 2017 IEEE International Conference on Computer Vision Workshops (ICCVW). IEEE, 2017. (Year: 2017).*

Suwannakhun, Sirimonpak, and Patasu Daungmala. "Estimating pig weight with digital image processing using deep learning." 2018 14th International Conference on Signal-Image Technology & Internet-Based Systems (SITIS). IEEE, 2018. (Year: 2018).*

Jun, Kyungkoo, Si Jung Kim, and Hyun Wook Ji. "Estimating pig weights from images without constraint on posture and illumination." Computers and Electronics in Agriculture 153 (2018): 169-176. (Year: 2018).*

Yang, Qiumei, Deqin Xiao, and Sicong Lin. "Feeding behavior recognition for group-housed pigs with the Faster R-CNN." Computers and electronics in agriculture 155 (2018): 453-460. (Year: 2018).*

Psota, Eric T., et al. "Multi-pig part detection and association with a fully-convolutional network." Sensors 19.4 (2019): 852. (Year: 2019).*

Kashiha, Mohammadamin, et al. "Automatic weight estimation of individual pigs using image analysis." Computers and Electronics in Agriculture 107 (2014): 38-44. (Year: 2014).*

Love, J. E., "Video Imaging for Real-Time Performance Monitoring of Growing-Finishing Pigs" (Doctoral dissertation), Aug. 31, 2012 (Aug. 31, 2012).

* cited by examiner

MONITORING LIVESTOCK IN AN AGRICULTURAL PEN

CROSS REFERENCE TO RELATED APPLICATIONS

This application is a National Phase of PCT Application No. PCT/IL2019/050706 having International filing date of Jun. 25, 2019, which claims the benefit of priority under 35 U.S.C. § 119 (e) of U.S. Provisional Patent Application No. 62/689,251 filed on Jun. 25, 2018 and U.S. Provisional Patent Application No. 62/827,203 filed on Apr. 1, 2019, both entitled "MONITORING LIVESTOCK IN AN AGRICULTURAL PEN." The contents of the above applications are all incorporated by reference as if fully set forth herein in their entirety.

FIELD

The present disclosure relates to computer imaging.

BACKGROUND

Modern farms grow livestock animals of a single species, with the goal of maintaining the animals in the a under near optimal physical conditions for maximum growth and yield. Such physical conditions may include an animal's physical state, such as weight and health condition, as well as the pen's physical condition, such as the ventilation and proper functionality of the pen's equipment, such as feeding equipment, water equipment and the like. Accordingly, farms engage in continued monitoring of feeding, environmental conditions, health, weight, growth, and reproduction of the livestock.

The treatment of the livestock is mostly performed by humans taking care of feeding, weighing, controlling environment physical states such as ventilation, identifying the health of the animals, detecting disease and death and the like.

Weight is an important indicator of the health and worth of an animal in the pen. Farmers need to pay close attention to the weight of the animal in order to be profitable. Growing an animal beyond a certain weight may dramatically reduce their market value, causing the farmer to lose significant revenue. Current procedures of weighing animals are inefficient as they are time and labor consuming. In addition, weighing animals using a weight scale, puts the animals under stress and reduces their rate of growing. Therefore, farmers tend to take decisions related to animals' weight, without actually weighing them and knowing their actual weight, decisions that may lead to loss of profit.

Late detection of the physical state of animals in the pen, such as pregnancy, labor and/or disease, may lead to maltreatment, high mortality rate of new born and epidemics.

The foregoing examples of the related art and limitations related therewith are intended to be illustrative and not exclusive. Other limitations of the related art will become apparent to those of skill in the art upon a reading of the specification and a study of the figures.

SUMMARY

The following embodiments and aspects thereof are described and illustrated in conjunction with systems, tools and methods which are meant to be exemplary and illustrative, not limiting in scope.

There is provided, in an embodiment, a method comprising: receiving an image of a scene comprising one or more animals; defining region boundaries for each of said one or more animals; evaluating a suitability of each of said region boundaries for further processing, based, at least in part, on a predetermined set of parameters; and determining at least one of: (i) a physical state of at least some of said one or more animals, based, at least in part, on said further processing, and (ii) an identity of at least some of said one or more animals.

There is also provided, in an embodiment, a system comprising: at least one hardware processor; and a non-transitory computer-readable storage medium having stored thereon program instructions, the program instructions executable by the at least one hardware processor to: receive an image of a scene comprising one or more animals, define region boundaries for each of said one or more animals, evaluate a suitability of each of said region boundaries for further processing, based, at least in part, on a predetermined set of parameters, and determine at least one of: (i) a physical state of at least some of said one or more animals, based, at least in part, on said further processing, and (ii) an identity of at least some of said one or more animals.

There is further provided, in an embodiment, a computer program product comprising a non-transitory computer-readable storage medium having program instructions embodied therewith, the program instructions executable by at least one hardware processor to: receive an image of a scene comprising one or more animals; define region boundaries for each of said one or more animals; evaluate a suitability of each of said region boundaries for further processing, based, at least in part, on a predetermined set of parameters; and determine at least one of: (i) a physical state of at least some of said one or more animals, based, at least in part, on said further processing, and (ii) an identity of at least some of said one or more animals.

In some embodiments, said scene comprises a livestock group housing environment.

In some embodiments, said image is captured from an overhead perspective in relation to said one or more animals.

In some embodiments, with respect to each of said identified region boundaries, said set of parameters comprises at least one of: an overhead perspective angle of a region boundary in said image, a location of a region boundary in said image relative to an acquisition point of said image, visibility of said animal in said scene, location of said animal in said scene, occlusion of said animal in said scene, and a bodily posture of said animal in said scene.

In some embodiments, said evaluating comprises assigning a suitability score to each of said region boundaries, and wherein said further processing is only performed when said suitability score assigned to a region boundary exceeds a specified threshold.

In some embodiments, said defining comprises applying a machine learning detection algorithm, and wherein said machine learning detection algorithm is trained using a training set comprising: (i) a plurality of images of scenes, wherein each of said scenes comprises one or more animals; and (ii) labels associated with each of said one or more animals in said images.

In some embodiments, said further processing comprises identifying, with respect to each of said animals, segment boundaries associated with a bodily trunk of said animal.

In some embodiments, said segment boundaries associated with said bodily trunk of said animal exclude at least a head of said animal, a tail of said animal, and one or more limbs of said animal.

In some embodiments, said segment boundaries associated with said bodily trunk of said animal comprises applying a trained machine learning segmentation algorithm, and wherein said machine learning segmentation algorithm is trained using a training set comprising: (i) a plurality of images of animals, wherein said images are captured from an overhead perspective; and (ii) labels associated with segment boundaries of at least some of a bodily trunk, a head, a tail, and one or more limbs of each of said animal in said plurality of images.

In some embodiments, said determining of said physical state is based, at least in part, on a comparison between said segment boundaries associated with said bodily trunk of each of said animals and reference data.

In some embodiments, said determining of said physical state comprises applying a trained machine learning algorithm, and wherein said machine learning algorithm is trained using a training set comprising: (i) a plurality of images of animal trunks, wherein said images are captured from an overhead perspective; and (ii) labels associated with said physical state.

In some embodiments, with respect to each of said animals, said physical state is at least one of developmental stage, volume, weight, surface parameters, color, status, health, maturation, and similarity of said animal.

In some embodiments, said determining of said identity of at least some of said one or more animals is based, at least in part, on: (i) detecting an identification area associated with each of said region boundaries, and (ii) matching said detected identification area with a known identity.

In some embodiments, said identification area is located at a specified bodily region of said animal.

In some embodiments, said identification area comprises one or more of: one or more colored tags, a grayscale tag, a tattoo, a barcode, a tag with text, a tag with numbers, and a quick response (QR) code.

In some embodiments, said one or more animals are a population of animals of the same type and breed.

In some embodiments, said animal is selected from the group of livestock animals consisting of: cattle, cows, pigs, sheep, and goats.

In some embodiments, the method further comprises, and the program instructions are further executable to (i) receiving a sequence of images of said scene, and (ii) tracking at least one of said one or more animals in said sequence of images.

In some embodiments, said sequence of images is a video stream.

In some embodiments, said tracking is based on at least one of (i) a defined region boundary, (ii) a segment boundary, or (iii) an identification area associated with said at least one of said one or more animals.

In addition to the exemplary aspects and embodiments described above, further aspects and embodiments will become apparent by reference to the figures and by study of the following detailed description.

BRIEF DESCRIPTION OF THE DRAWINGS

The disclosure will now be described in relation to certain examples and embodiments with reference to the following illustrative figures so that it may be more fully understood. In the drawings.

Figure 1A:
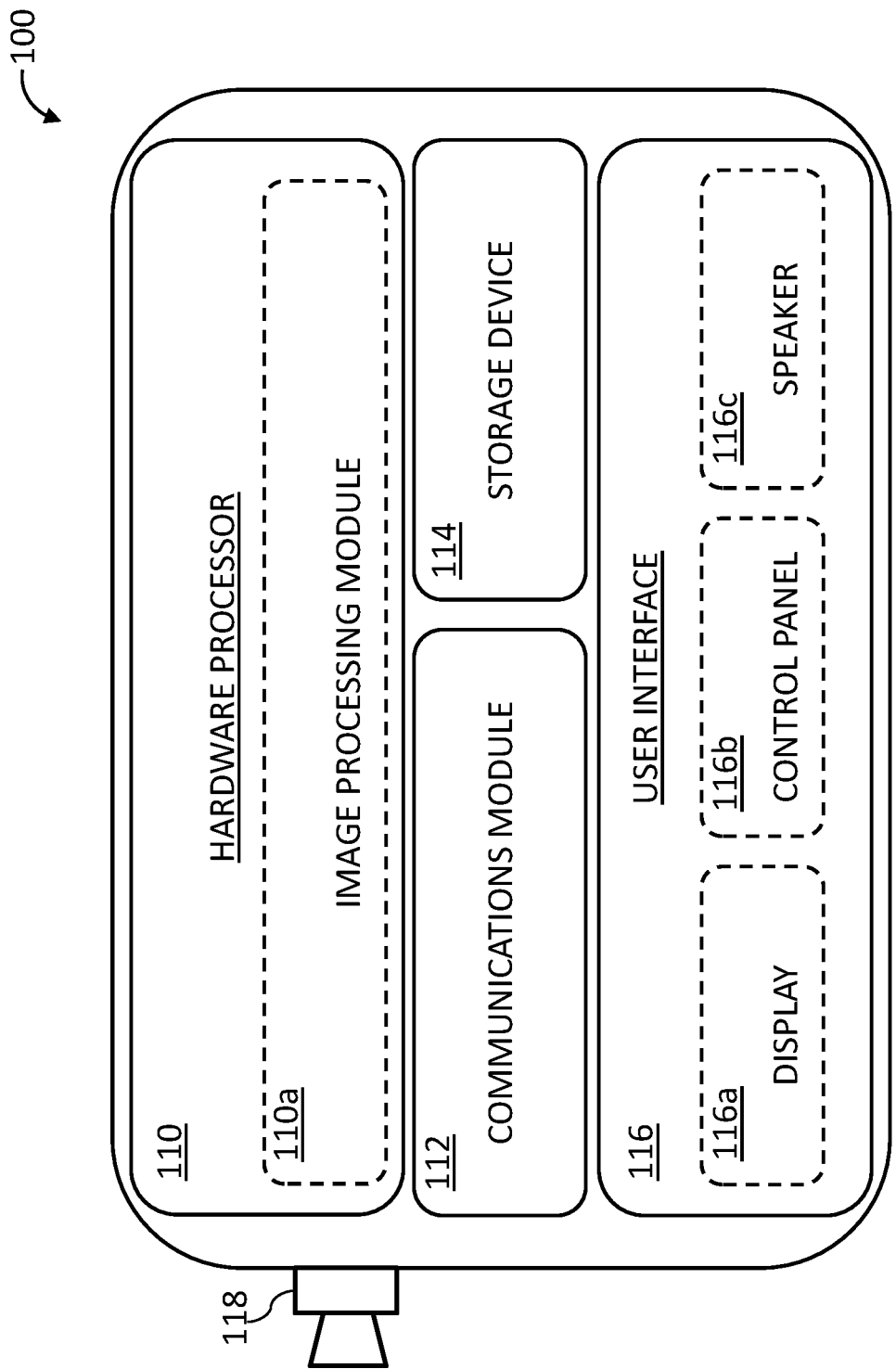
FIG. 1A is a block diagram of an exemplary system for automated identifying an individual animal in a livestock population environment, and determining one or more physical, developmental and/or wellbeing state parameters, according to embodiments of the invention.

It will be appreciated that for simplicity and clarity of illustration, elements shown in the figures have not necessarily been drawn to scale. For example, the dimensions of some of the elements may be exaggerated relative to other elements for clarity. Further, where considered appropriate, reference numerals may be repeated among the figures to indicate the same or analogous elements.

DETAILED DESCRIPTION

In the following description, various aspects of the present invention will be described. For purposes of explanation, specific configurations and details are set forth in order to provide a thorough understanding of the present invention. However, it will also be apparent to one skilled in the art that the present invention may be practiced without all the specific details presented herein. Furthermore, well known features may be omitted or simplified in order not to obscure the present invention.

Methods and systems according to embodiments of the present invention are directed at providing an automated computerized system for (i) identifying an individual animal in a livestock population environment, and (ii) determining one or more physical, developmental and/or wellbeing state parameters with respect to the identified animal.

In some embodiments, the livestock population comprises, e.g., cattle, cows, dairy cows, bulls, calves, pigs, sows, boars, piglets, horses, sheep, goats, and/or deer. In some embodiments, the population of animals is of the same type, breed and/or race.

In some embodiments, the present disclosure provides for the calculation and/or estimation of a plurality of parameters associated with a physical, developmental and/or wellbeing state of a livestock animal, including, for instance, individual identity, size, volume, weight, surface parameters, color, status, health, maturation, similarity, behavioral state, mood, visual attention, and other related parameters.

In some embodiments, the livestock animals are housed is a group housing environment, e.g., a pen, feeding area, and/or a similar enclosure for housing a plurality of animals. In some embodiments, the present disclosure provides for acquiring, by an imaging device, one or more images, and/or a video stream of video images, of the housing environment. In some embodiments, the images are acquired from an overhead perspective, such that the images capture substantially a back region of each animal.

In some embodiments, the present disclosure provides for detecting one or more animals in the images, using one or more object detection methods. In some embodiments, the present disclosure is configured to define boundaries of each animal in an image, e.g., by way of a bounding box. As used herein, the term "bounding box" refers to an area in an image that envelops content. For example, one or more bounding boxes can be, e.g., a square or rectangular frame around a recognized object in an image.

In some embodiments, the present disclosure may then be configured for evaluating a suitability of each detected animal in the image for further processing, e.g., by assessing at least one of completeness of the animal in the bounding box (e.g., when an animal is only partially represented in the image), animal bodily pose (e.g., standing, lying down), visibility, occlusion (e.g., when animals stands close to one another, or when one animal steps over another), and/or location relative to the imaging device, which determines a perspective angle of the animal in the image.

In some embodiments, the present disclosure may be configured to assign a suitability score to each animal detected in the image, wherein further processing of the image may be provided for when the suitability score exceeds, e.g., a specified threshold.

In some embodiments, further processing of the images may comprise, e.g., segmenting each bounding box associated with an animal in the images into segments associated with e.g., a bodily trunk of the animal, a head, limbs, and a tail of the animal.

In some embodiments, the present disclosure further provides for determining a physical, developmental and/or wellbeing state of the animal based, at least in part, on a comparing between a segment associated with a bodily trunk of the animal and reference data. In some embodiments, a physical, developmental and/or wellbeing with respect to an may include, for instance, size, volume, weight, surface parameters, color, status, health, maturation, similarity, behavioral state, mood, visual attention, and other related parameters In some embodiments, the present disclosure may be further configured for identifying one or more animals detected in the images based, e.g., on known animal identities. In some embodiments, animal identification is based, at least in part, on detecting an identification area associated with the bounding box of the animal, and matching the detected identification area with known identify. In some embodiments, the identification area may be located at a specified bodily region of said animal. In some embodiments, the identification area comprises at least one of: one or more colored tags, a tattoo, a barcode, a tag with text and/or numbers, and/or a quick response (QR) code.

FIG. 1 is a block diagram of an exemplary system 100 for automated identification of an individual animal in a livestock population environment, and determining one or more physical, developmental and/or wellbeing state parameters with respect to the identified animal. System 100 as described herein is only an exemplary embodiment of the present invention, and in practice may have more or fewer components than shown, may combine two or more of the components, or a may have a different configuration or arrangement of the components. The various components of system 100 may be implemented in hardware, software or a combination of both hardware and software. In various embodiments, system 100 may comprise a dedicated hardware device, such as a mobile device, a cellphone, a digital camera, and the like.

In some embodiments, system 100 may comprise a hardware processor 110, communications module 112, memory storage device 114, user interface 116, AND imaging device 118, and a light source 120. System 100 may store in a non-volatile memory thereof, such as storage device 114, software instructions or components configured to operate a processing unit (also "hardware processor," "CPU," or simply "processor), such as hardware processor 110. In some embodiments, the software components may include an operating system, including various software components and/or drivers for controlling and managing general system tasks (e.g., memory management, storage device control, power management, etc.) and facilitating communication between various hardware and software components.

In some embodiments, non-transient computer-readable storage device 114 (which may include one or more computer readable storage mediums) is used for storing, retrieving, comparing, and/or annotating captured image frames. Image frames may be stored on storage device 114 based on one or more attributes, or tags, such as a time stamp, a user-entered label, or the result of an applied image processing method indicating the association of the frames, to name a few.

The software instructions and/or components operating hardware processor 110 may include instructions for receiving and analyzing multiple image frames captured by imaging device 118. For example, hardware processor 110 may comprise image processing module 110a, which receives one or more images and/or image streams from imaging device 118 and applies one or more image processing algorithms thereto. In some embodiments, image processing module 110a and/or machine learning module 110b comprise one or more algorithms configured to perform object detection, segmentation, recognition, identification, and/or classification in images captured by imaging device 118, using any suitable image processing technique. The image streams received by the image processing module 110a may vary in resolution, frame rate (e.g., between 15 and 35 frames per second), format, and protocol according to the characteristics and purpose of their respective source device. Depending on the embodiment, the image processing module 110a can route image streams through various processing functions, or to an output circuit that sends the processed image stream for presentation, e.g., on a display 116a, to a recording system, across a network, or to another logical destination. In image processing module 110a, the image stream processing algorithm may improve the visibility and reduce or eliminate distortion, glare, or other undesirable effects in the image stream provided by an imaging device. An image stream processing algorithm may reduce or remove fog, smoke, contaminants, or other obscurities present in the image stream. The image stream processing module 110a may apply image stream processing algorithms alone or in combination.

In some embodiments, system 100 comprises a communications module (or a set of instructions), a contact/motion module (or a set of instructions), a graphics module (or a set of instructions), a text input module (or a set of instructions), a Global Positioning System (GPS) module (or a set of instructions), voice recognition and/or and voice replication module (or a set of instructions), and one or more applications (or sets of instructions).

For example, a communications module 112 may connect system 100 to a network, such as the Internet, a local area network, a wide area network and/or a wireless network. Communications module 112 facilitates communications with other devices over one or more external ports, and also includes various software components for handling data received by system 100.

In some embodiments, a user interface 116 of system 100 comprises a display monitor 116a for displaying images, a control panel 116b for controlling system 100, and a speaker 116c for providing audio feedback. In some variations, display 116a may be used as a viewfinder and/or a live display for either still and/or video image acquisition by imaging device 118. The image stream presented by display 116a may be one originating from imaging device 118.

Imaging device 118 is broadly defined as any device that captures images and represents them as data. Imaging device 118 may include a 2D or 3D camera and/or a camera configured to capture images in which animals may be detected and/or identified even in low illumination physical states (e.g., at night). One or more imaging devices 118 may be installed in a livestock housing environment, so that multiple areas of interest (e.g., feeding area and drinking area) can be captured, typically at known angles. Imaging device 118 may be installed, for example, on the ceiling of the pen so that it can capture top view images of the whole pen or of one or more areas of interest, as illustrated in FIG. 1B.

Imaging devices 118 may be optic-based, but may also include depth sensors, radio frequency imaging, ultrasound imaging, infrared imaging, and the like. In some embodiments, imaging device 118 may be configured to detect RGB (red-green-blue) spectral data. In other embodiments, imaging device 118 may be configured to detect at least one of monochrome, ultraviolet (UV), near infrared (NIR), and short-wave infrared (SWIR) spectral data. In some embodiments, imaging device 118 comprises a digital imaging sensor selected from the group consisting of silicon-based detectors, complementary metal-oxide-semiconductor (CMOS), charge-coupled device (CCD), Indium gallium arsenide (InGaAs), and polarization-sensitive sensor element. Imaging device 118 may further comprise, e.g., zoom, magnification, and/or focus capabilities. Imaging device 118 may also comprise such functionalities as color filtering, polarization, and/or glare removal, for optimum visualization. Imaging device 118 may further include an image stream recording system configured to receive and store a recording of an image stream received, processed, and/or presented through system 100.

In some embodiments, system 100 includes one or more user input control devices, such as a physical or virtual joystick, mouse, and/or click wheel. In other variations, system 100 comprises one or more of a peripherals interface, RF circuitry, audio circuitry, a microphone, an input/output (I/O) subsystem, other input or control devices, optical or other sensors, and an external port. System 100 may also comprise one or more sensors, such a proximity sensors and/or accelerometers. Each of the above identified modules and applications correspond to a set of instructions for performing one or more functions described above. These modules (i.e., sets of instructions) need not be implemented as separate software programs, procedures or modules, and thus various subsets of these modules may be combined or otherwise re-arranged in various embodiments.

System 100 described herein is only an exemplary embodiment of the present system, and may have more or fewer components than shown, may combine two or more components, or a may have a different configuration or arrangement of the components. The various components of system 100 may be implemented in hardware, software or a combination of both hardware and software, including one or more signal processing and/or application-specific integrated circuits. In various embodiments, system 100 may comprise a dedicated hardware device, or may form an addition to or extension of an existing medical device, such as a colposcope. In addition, aspects of the present system which can be implemented by computer program instructions, may be executed on a general purpose computer, a special-purpose computer, or other programmable data processing apparatus.

In some embodiments, system 100 may be configured to control one or more devices, appliances, and/or system associated with the livestock environment and the operation of the pen, such as a ventilation system; a feeding system; painting equipment to mark (with paint) a specific animal; a heating system; and the like. In some embodiments, additional devices that may be controlled by system 100 may include, e.g., a device maintaining a database to which data may be written; or a device running applications which may include, for example, a messaging application In some embodiments, system 100 may further comprise a sensors module which may include a sensor that provides information regarding environmental conditions (e.g., temperature, humidity) and/or animal behavior, movement, location, and/or speed.

In some embodiments, a user application may be installed on any user device, such as a computer or a mobile device, and may be in communication with system 100, e., through communications module 112. The user application may provide information to the user regarding each individual animal in the pen and the entire pen, entire buildings and/or entire farms, at a given time and/or over time. In addition, the user application may provide predictions regarding animals' physical states (e.g. weight, health, etc.), e.g., based on data stored in a database. The user application may, in addition, provide alerts and notifications regarding alarming animal's or pen's physical states. In one example, the user application may include or may be connected to user interface 116, for displaying e.g., images, instructions and/or notifications (e.g., via text or other content displayed on the monitor). The user interface 116 may also be designed to receive input from an external user. For example, the user interface device may include a monitor and keyboard and/or mouse and/or touch screen, to enable an external user to interact with the system. In some embodiments the user interface may include a light that may light up or change color or another indicator, such as an audio player to emit a sound. Optionally, the user interface may be provided on a multi-purpose device such as a smartphone, tablet or personal computer.

FIGS. 2A, 2B, 2C and 2D, to which reference is now made, are schematic illustrations of monitoring process 200, constructed and operative in accordance with embodiments of the present invention.

In one embodiment (FIG. 2A), monitoring process 200 may receive a sequence of images 201 (e.g., 2D images), process each of images 201 and create an output comprising at least one of a physical state of at least some of the animals in the image, and/or an identity of at least some of the animals.

Figure 1B:
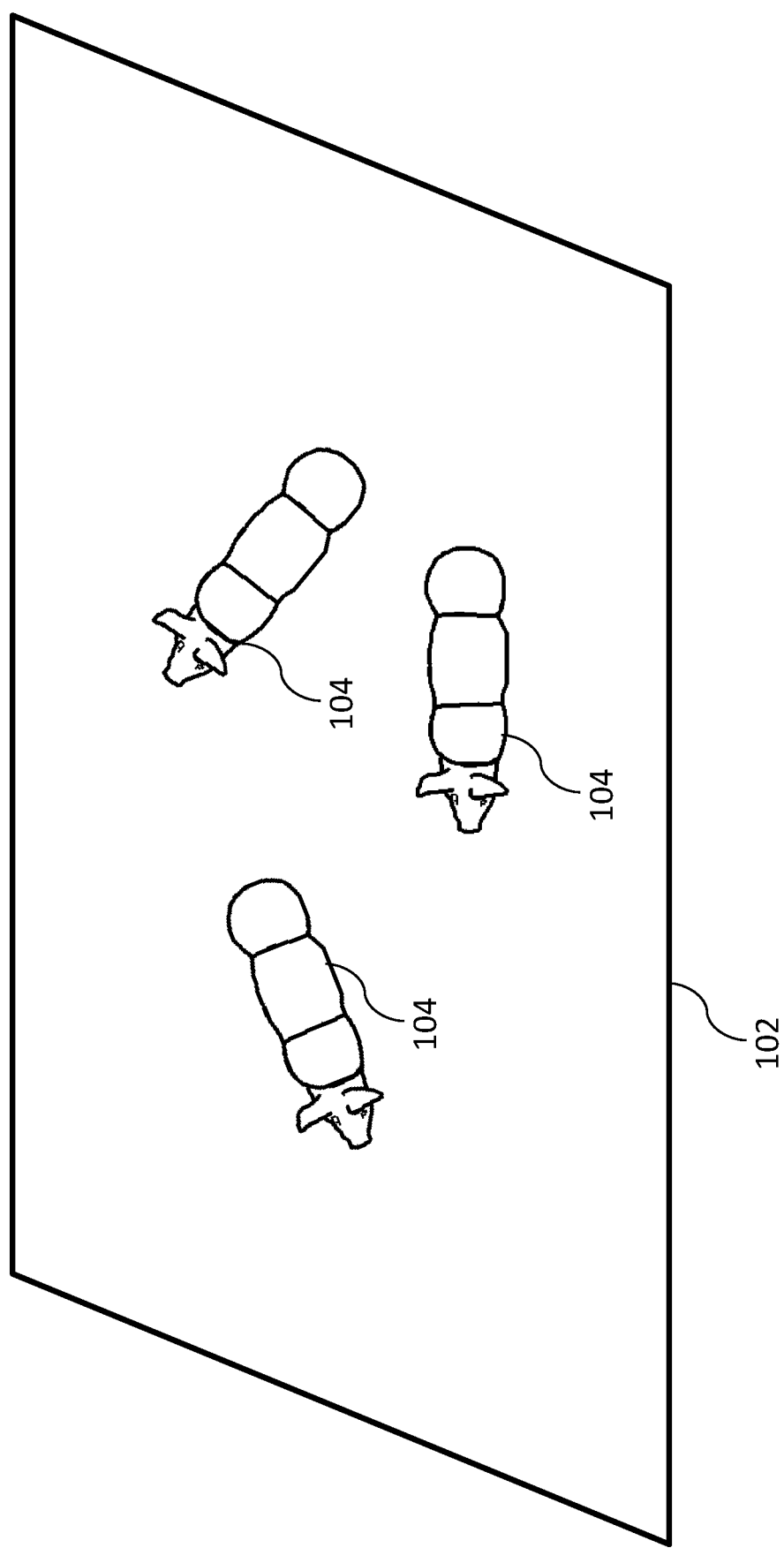
FIG. 1B is a top view image of an animal.

In one embodiment monitoring process 200 includes operating, e., image processing module 110a in FIG. 1A, to apply a detection module 210 for detecting individual animals from an image; an identification module 220 for assigning an identity to individual animals; an assessment module 230 for assessing a physical state of an animal and/or of a pen; and an output module 240 to generate an appropriate output, based on the assessed identification and physical state.

Figure 2A:
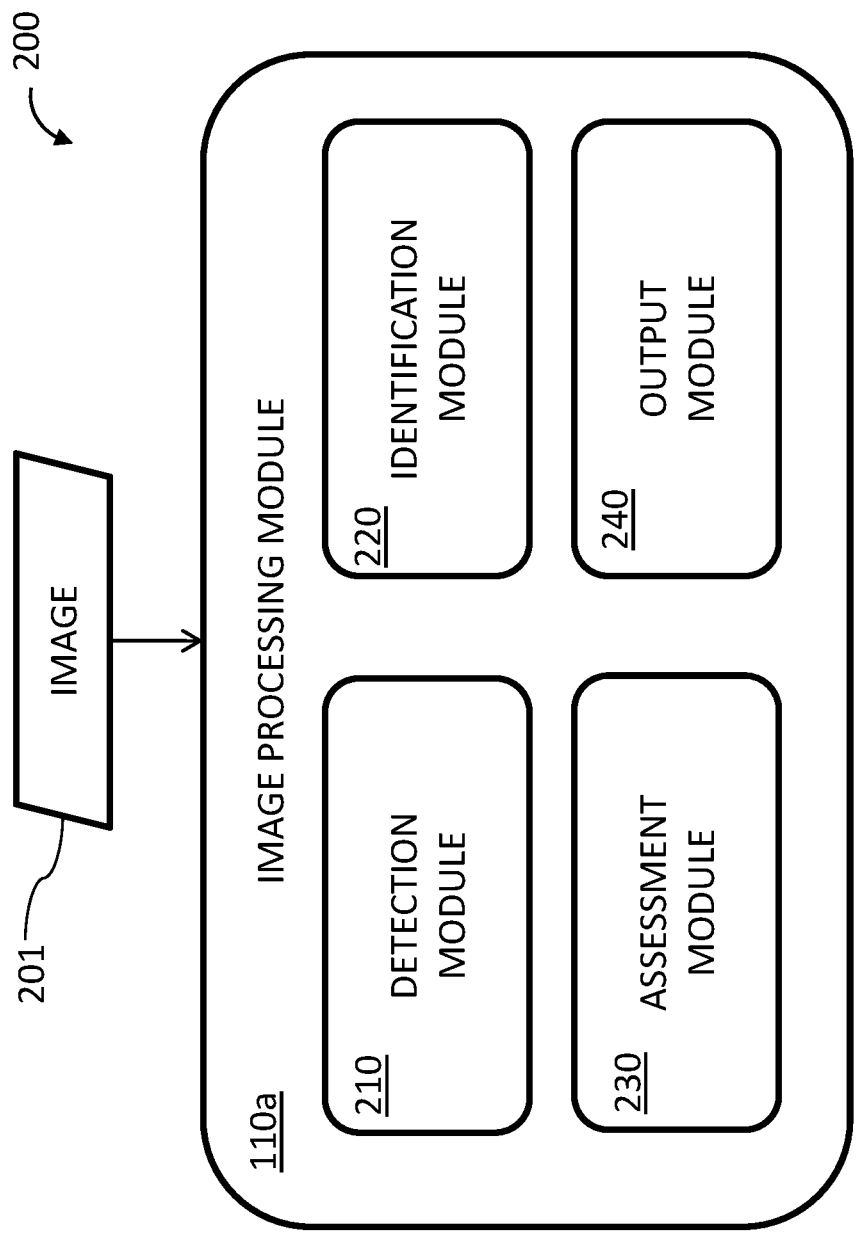
FIGS. 2A, 2B, 2C and 2D are schematic illustrations of processes for identifying an individual animal in a livestock population environment, and determining one or more physical, developmental and/or wellbeing state parameters, according to embodiments of the invention.
Figure 2B:
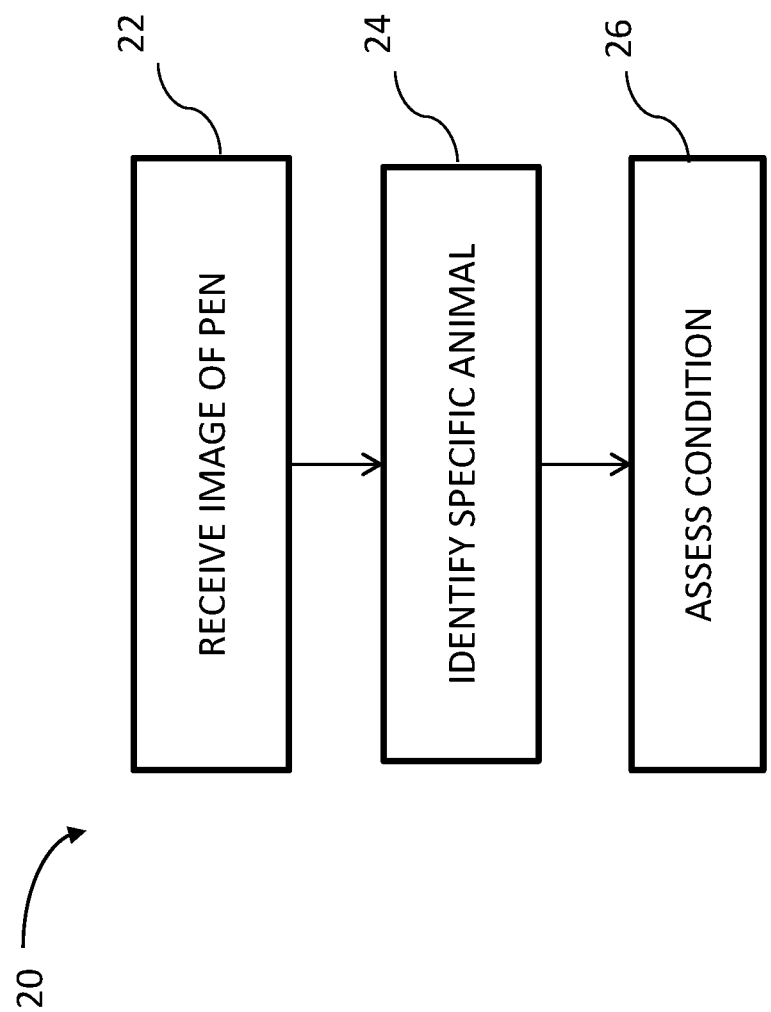

In one embodiment, illustrated in FIG. 2B, monitoring process 200 may implement flow 20. In step 22 monitoring process 200 may receive an image of an area of the pen. In step 24 monitoring process 200 may identify, via identification module 220, a specific animal based on pixels of the image, which are associated with the specific animal. In step 26 monitoring process 200 may assess from the image, via assessment module 230, a physical state related to the identified animal.

Figure 2C:
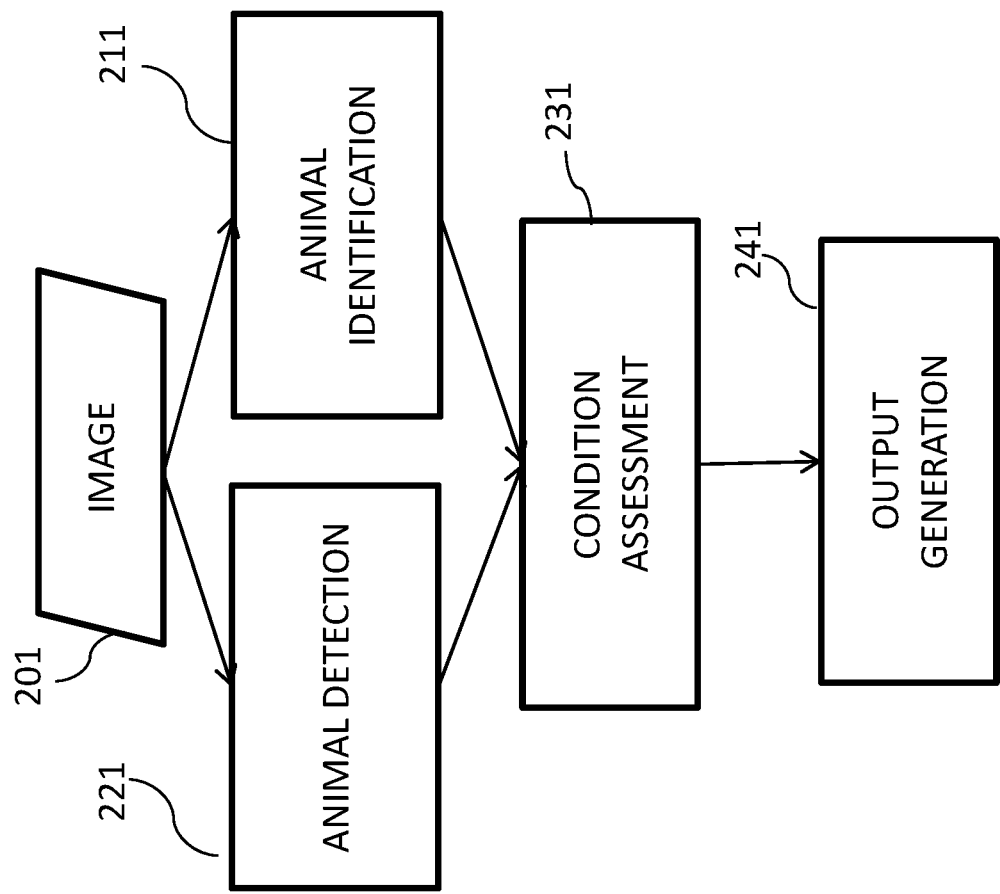
Figure 2D:
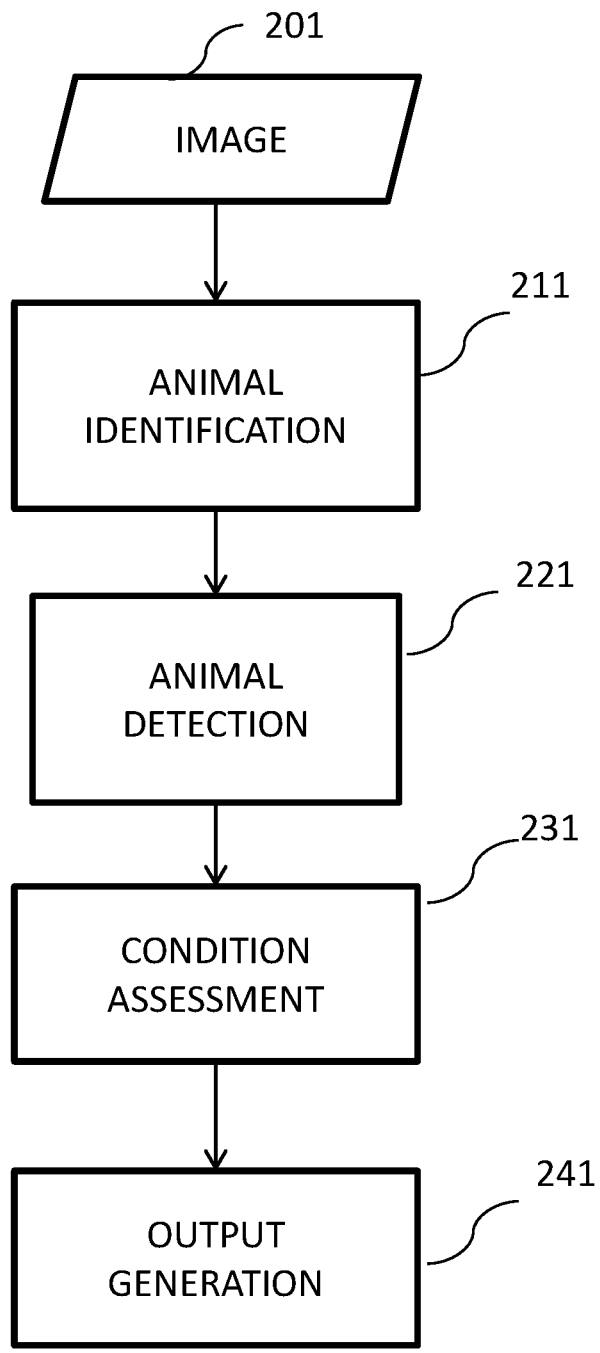

In one embodiment, illustrated in FIGS. 2C and 2D image 201 may be a top view image of an area in a pen on which both detection module 210 and identification module 220 may operate concurrently. In step 211 detection module 210 may detect and segment the different animals present in image 201 and in step 221 identification module 220 may identify each specific animal in image 201. After each animal is detected, segmented and identified, in step 231 assessment module 230 may assess a physical state of each animal or a physical state of the pen and in step 241, output generation module 240 may create and send an output.

The order of steps of detecting (and segmenting) and identifying the animals in image 201 may vary in different embodiments. In one embodiment, detection module 210 may first operate in step 221 to detect the different animals present in image 201 and only then identification module 220 may operate in step 211 to identify each specific animal (FIG. 2C). In another embodiment, monitoring process 200 may first activate identification module 220 to first identify each specific animal and then activate detection module 210 to detect and segment the different animals.

Figure 3A:
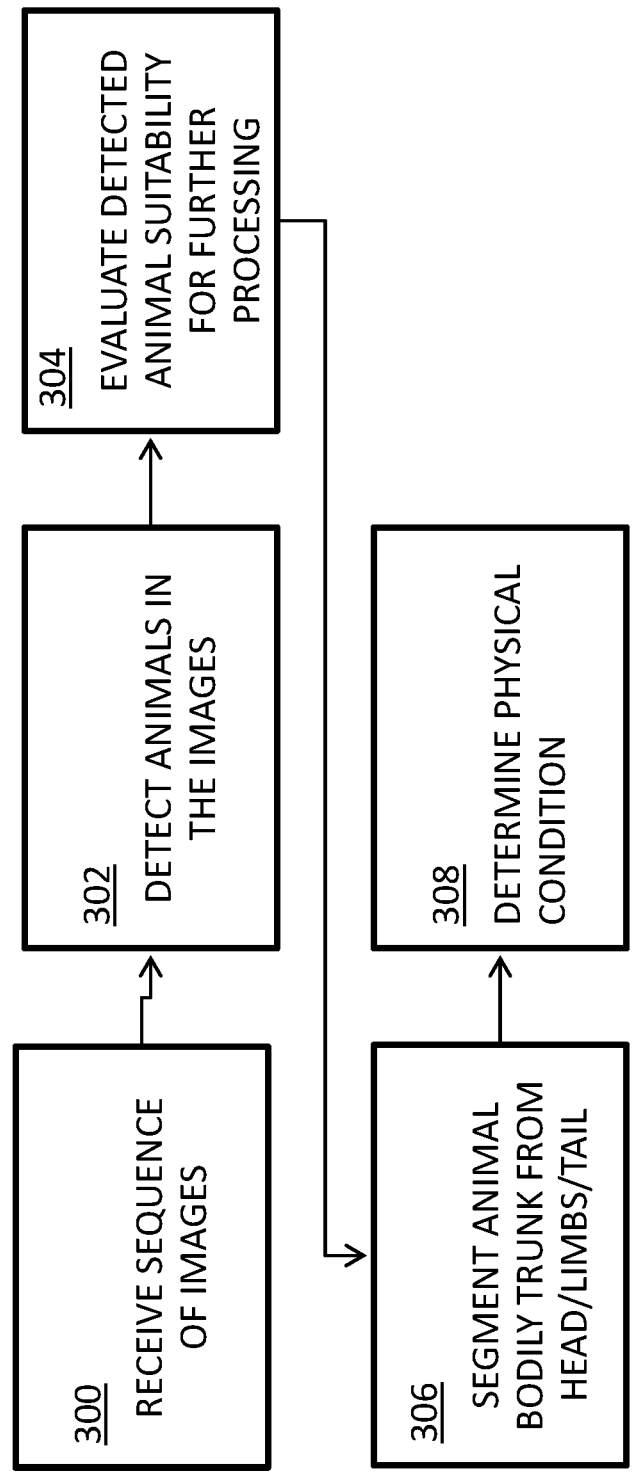
FIGS. 3A and 3B are flowcharts of the functional steps is a process for identifying an individual animal in a livestock population environment, and determining one or more physical, developmental and/or wellbeing state parameters, according to embodiments of the invention.

The functional steps is a process for detection of an animal in an image will now be described with reference to FIG. 3A.

At step 300, a system such as system 100 in FIG. 1A, may receive a sequence of images depicting a top view of an area in a livestock pen.

In some embodiments, at step 302, image processing module 110a may be configured to detect animals (e.g., pigs) in an image by, e.g., first defining a bounding box associated with each animal in the image. In some embodiments, image processing module 110a may use multiple segmentation procedures, such as a trained multi-region convolutional neural network (MR-CNN) or any other suitable shape detection and segmentation algorithm. A MR-CNN may be trained, for example, to (i) classify images to ones containing animals and ones not containing animals, (ii) in the images containing animals, may separate between animals by creating a bounding shape around each animal, and (iii) determine, for each pixel in the image, whether it belongs to a animal, a background, or to another animal. Other multiple segmentation procedures may be employed by image processing module 110a to detect the animals in the image, including other machine learning algorithms that may be trained to detect animals.

Assessment module 230 may assess an animal's physical state from an image (or set of images) 201, typically, based on detection and segmentation processes carried out by image processing module 110a and/or by applying image analysis algorithms (such as, shape detection and motion detection algorithms) on the image (or images). In some embodiments, assessment module 230 may receive, as input, a vector including information extracted from image 201 such as pixels, their distance from the middle of the image, their x and y coordinates, center of gravity of a detected animal (e.g., based on the animals' bounding shape) and the like, and may be trained on such vectors using machine learning algorithms and/or otherwise use such vectors (e.g., as described below) to assess a physical state of the animal from the image.

In some embodiments, the algorithm may be trained on a training set comprising a plurality of images of a top view of an area in a livestock pen comprising a plurality of animals. In some embodiments, the training set images may be labeled with suitable labels with respect to the presence of animals in the images, and/or areas associated with 'animal' and 'background.'

In some embodiments, animal detection may be carried out on images obtained from a 3D camera and/or from an IR camera, using known techniques.

In some embodiments, at step 304, after correct definition of a bounding box associated with each of the animals on the image, the present disclosure may be configured to apply election criteria on the detected animals and select only those animals complying with one or more criteria for further processing. The criteria may be associated with the detected shape, (which may indicate the physical state of the identified animal). For example, criteria related to the shape may include criteria related to the bounding shape and/or to other shape parameters of the animal. Criteria relating to the bounding shape may include e.g., "having a complete bounding shape in the image"; "the bounding shape being located within a specified angle or distance from the camera's vertical" (e.g., directly beneath the camera); "the bounding shape includes the entire animal"; "the shape of the bounding shape is a specific shape" (e.g. the shape of the a bounding shape should be a rectangle or ellipse and not a square or circle, when dealing with animals) and the like. Criteria relating to the shape of the detected animal may include, e.g., the outline of the animal, its rotation (i.e. the angle relative to the camera axis) its posture (i.e. whether it is standing, siting, reclining, etc.) and the like. In some embodiments, the selection criteria may be based on a plurality of parameters, including, but not limited to, a completeness of the animal in the bounding box (e.g., when an animal is only partially represented in the image), animal bodily pose (e.g., standing, lying down), visibility, occlusion (e.g., when animals stands close to one another, or when one animal steps over another), and/or location relative to the imaging device, which determines a perspective angle of the animal in the image.

For example, in some embodiments, a machine learning classifier may be trained to classify animal shapes to determine suitability for further processing. The purpose of the suitability classifying stage is to discard animals in the images which are partial, incomplete, occluded, located too far from a point of acquisition of the images, and/or in too close a proximity to other animals, because such animals may not be appropriately segmented in subsequent stages. In some embodiments, the machine learning classifier is trained on a training set comprising a plurality of images of a top view of an area in a livestock pen comprising a plurality of animals, wherein each of the animals is labelled according to, e.g. its body shape (e.g., animals that are lying down on the ground may present a body shape that is more rounded, as compared to animals that are standing up); whether it appears as a whole or partial animal in the image; whether it is in contact engagement with another animal; whether it is occluded by another animal and/or another object; and/or based on its location relative to the point from which the image was acquired, which affect a perspective angle of the animal in the image.

The trained classifier may then be applied to one or more images acquired as in step 300, to predict a suitability of each of the animals in the image for further processing. In some embodiments, the trained classifier may assign a suitability score, wherein further processing of the image may be provided for when the suitability score exceeds, e.g., a specified threshold.

In some embodiments, at step 306, the present disclosure may be configured to perform image segmentation to segment, e.g., a bodily trunk of each of the animals in the images from, e.g., a head, limbs, and a tail of the animal.

In some embodiments, the segmentation step may involve a process of semantic segmentation, which aims to recover image regions corresponding directly to objects in an image, by labeling each pixel in the image to a semantic category. In some cases, convolutional neural networks (CNNs), such as MR-CNN, can be used in image semantic segmentation.

In some embodiments, a machine learning segmentation algorithm may be trained on a training set comprising a plurality of images of a top view (i.e., back regions) of animals, wherein the regions in the images corresponding to the semantic classes 'bodily trunk,' 'head,' 'limbs,' and/or 'tail' are labelled in the images. The trained segmentation algorithm may then be applied to one or more images acquired as in step 300, to predict a corresponding class for each of the segments in the images.

In some embodiments, at step 308, an image comprising a segmented bodily trunk region of an animal may be processed to determine a physical state of the animal. In some embodiments, such physical state may be at least one of size, volume, weight, status, health, wellbeing, and/or maturation. In some embodiments, the determination is based, at least in part, on a comparison with reference data.

In some embodiments, a machine learning algorithm may be trained to predict one or more animal physical states on a training set comprising a plurality of images of bodily trunk segments of a plurality of animals, wherein each of segments is labelled according to, e.g., one or more physical state parameters associated with such animal. The trained machine learning algorithm may then be applied to one or more images acquired as in step 300, to predict a one or more physical state parameters associated with a target animal.

In one embodiment assessment module 230 may predict the weight of the pig by assigning a pixel-weight to a pixel belonging to the animal's body part and computing the animal's weight by using linear regression. Additional parameters (such as, number of pixels in the animal's body part, distance of each pixel from the center of the image, etc.) may be used to assess or predict an animal's weight, whereas a linear regression method may be used to find the best linear correlation of each parameter to a pixel-weight. For example, the body of the animal is larger and may contain more pixels in images of an animal at the periphery of the camera FOV than the body of that same animal in an image of the animal in the center of the camera FOV. Using a linear regression method the animal's weight can be adjusted to the location of the animal in the image. In some embodiments, additional parameters (e.g., as described above), may be used to train a neural network to assess a weight of an animal based on a body part of the animal in an image.

Machine learning methods may be trained to consider the angle of photography (e.g. ignore some pixels when the pig is located at the edge of the image, i.e. ignore those pixels belonging to the height projection and therefore should not be taken into account for the weight calculation), the shape and/or the location of the animal in the image and the like.

Since the animal moves in the pen, image 201 may capture only part of an animal in an image, or may capture the animal in different poses, some of which do not provide enough information needed for an assessment. In these cases, the assessment result may vary between consecutive images, for example when the animal is reclining, the image may include only a subset of the pixels needed to calculate its weight and the resultant assessment may be lower than the actual value.

When a sequence of images is provided, assessment module 230 may take into consideration the weight assessed in previous images of a tracked animal and improve the accuracy of the assessment of an animal's physical state. For example, assessment module 230 may compute an average between weights calculated for the tracked animal in different images in the sequence, calculate the median, ignore outliers, consider the assessed weight in a majority of images, and/or use any other statistical or non-statistical consideration while assessing the animal's weight based on a plurality of images of the animal. Assessment of weight may further be assisted by using information from previous images (e.g., images of the animal and/or of other animals in the same pen, captured within the past few days) stored in database 110, to smooth the weight assessment.

Figure 3B:
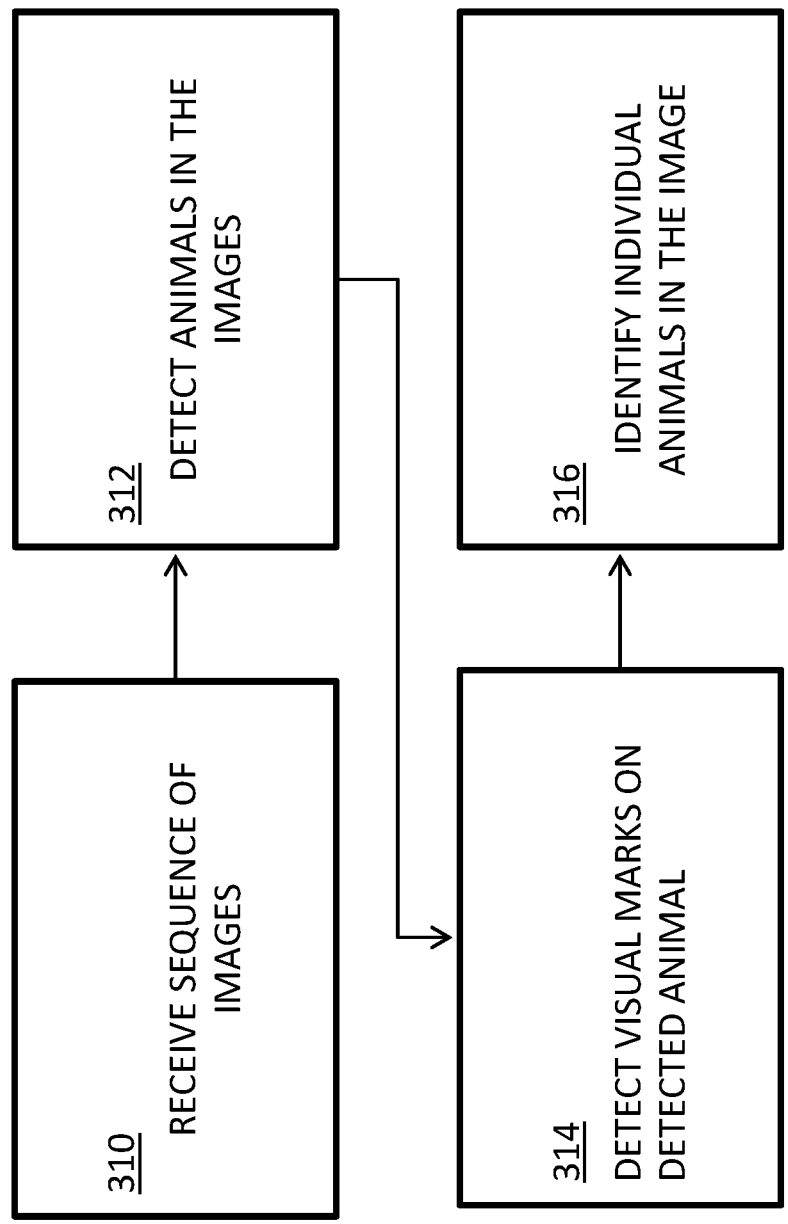

The functional steps is a process for identification of an individual animal in an image will now be described with reference to FIG. 3B. in some embodiments, the present disclosure is configured to identify individual and specific animals in an image, based on pixels of the image, the pixels associated with a specific animal. In one embodiment a visible mark associated with the specific animal, is detected in the image and is used to identify the specific animal.

At step 310, a system such as system 100 in FIG. 1A, may receive a sequence of images depicting a top view of an area in a livestock pen.

In some embodiments, at step 312, image processing module 110a may be configured to detect animals (e.g., pigs) in an image by, e.g., first defining a bounding box associated with each animal in the image. In some embodiments, image processing module 110a may use multiple segmentation procedures, such as a trained multi-region convolutional neural network (MR-CNN) or any other suitable shape detection and segmentation algorithm. A MR-CNN may be trained, for example, to (i) classify images to ones containing animals and ones not containing animals, (ii) in the images containing animals, may separate between animals by creating a bounding shape around each animal, and (iii) determine, for each pixel in the image, whether it belongs to a animal, a background, or to another animal. Other multiple segmentation procedures may be employed by image processing module 110a to detect the animals in the image, including other machine learning algorithms that may be trained to detect animals.

In one embodiment identification, at step 314, module 220 of image processing module 110a identifies a specific animal based on a visible mark and based on the location of the visible mark relative to the specific animal in the image. For example, the visible mark may be within the bounding shape of the animal or within a predetermined distance from the bounding shape. In another example, the visible mark may be on the animal's head. In one embodiment, the visible mark includes color tags attached to a specific location on the head of each animal. One or more color tags (possibly being of different shapes) may be attached to specific locations relative to the animal, e.g., in the ear of the animal, and/or in specific locations relative to each other, thus creating a plurality of unique combinations, each combination uniquely identifying a specific animal. In some embodiments the tags may be of different grey levels and/or the camera and/or image analysis of images of the pen may use greyscale image techniques, to avoid issues related to illumination in the pen. In some embodiments each color (or greyscale) tag may include one or more than one color or grey level. The different possible combination of color (or grey level) tags, their different shapes and their possible relation to each other is referred to herein as "color code".

Identification module 220 may detect the colors/shapes of the tags and provide the identification of each animal based on the color/shape combination. Identification module 220 may detect one or more visible color codes in a predetermined location relative to the specific animal in the image and may assign a unique identity to the animal based on this detection.

At step 316, in some embodiments, the visible mark may include a possibly transient pattern unique to a specific animal (e.g., a unique texture of the animal's skin at a specific location on the body of the animal, a unique pattern of dirt or other natural elements on the animal's skin, etc). Once a specific animal is detected and a transient or other visible mark is associated with the specific animal, the animal may be tracked throughout images of the pen and identified at any point based on the visible mark. In the case of a transient visible mark, the tracking and identification of the animal may be for a limited period of time, e.g., a few minute—a few hours.

Animals may be tracked throughout images of a pen by applying known tracking algorithms on the images, such as by using optical flow.

In some embodiments, a tracked animal may be identified in at least one image based on a color code. Once the animal is identified based on a color code, other, perhaps more easily visible, marks on the identified animal (such as the above mentioned transient patterns) may be associated with the identified animal, and the animal may then be identified in future images based on the more easily visible marks.

In some embodiments an animal may be identified by using face recognition algorithms. For example, one camera which is not located in the ceiling of the pen but rather at a location that enables capturing faces of the animals, provides images of the face of an animal at a certain location. That same animal may be simultaneously imaged by a camera located on the ceiling of the pen. Both images may be correlated to enable assigning an identity to the animal in the top view image, based on an image of that animal's face.

Figure 4A:
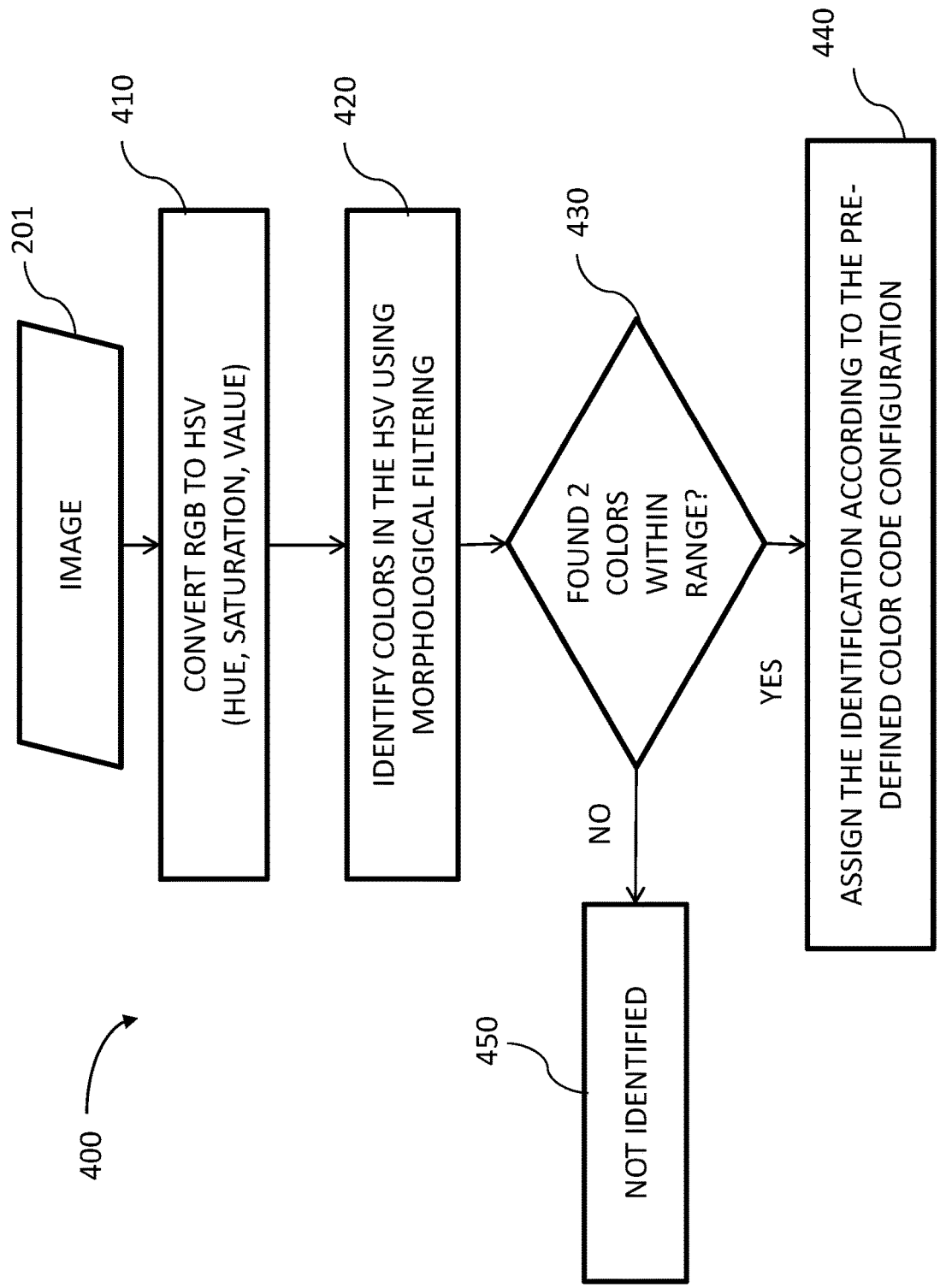
FIGS. 4A-4B exemplify processes run by detection and identification modules, according to embodiments of the invention.

FIG. 4A, to which reference is now made, is a schematic illustration of flow 400 possibly implemented by identification module 220 to identify a specific animal using visible marks, e.g., color marks, associated with the specific animal. Color mark identification flow 400 may identify animals marked with two colors in 2D images, coded with a red green blue (RGB) color model. The input to flow 400 may be RGB image 201. In step 410, identification module 220 may convert the RGB image to a hue, saturation, and value (HSV) model. In step 420 identification module 220 may identify colors in the HSV model using, for example, morphological filtering. In step 430 identification module 220 may check if two colors were detected within a predetermined distance range from each other, e.g. if the distance between two identified colors is smaller than a predefined value. If two colors were detected within the predetermined range, in step 440 identification module 220 may assign an identification to the specific animal according to a pre-defined color code configuration, for example, colors pink and blue comply with the color code of pig number X. If two colors were detected at a distance outside the predetermined range or if more than two colors were detected within the predetermined range, identification module 220 may declare in step 450 that the identification did not succeeded.

Figure 4B:
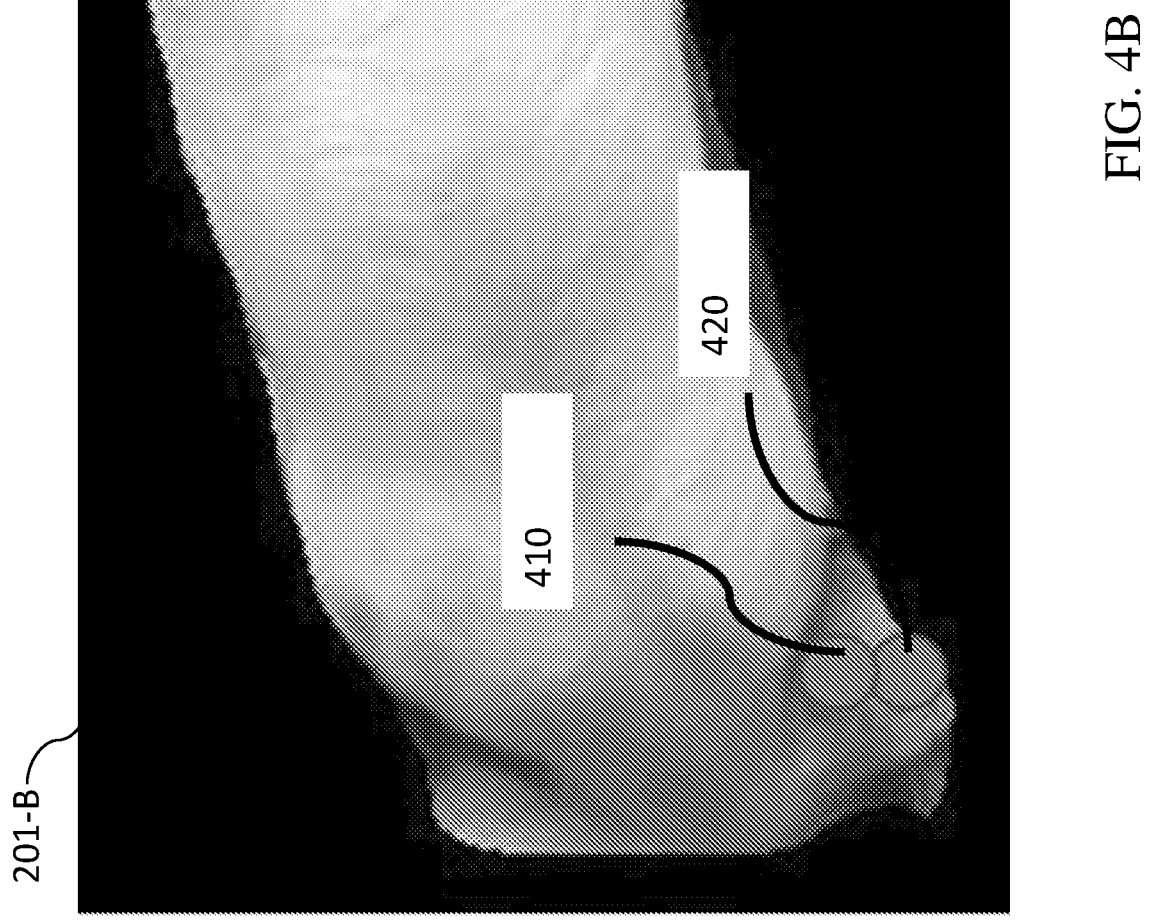

FIG. 4B, to which reference is now made, includes a sub-image 201B that includes one pig from the pigs captured in image 201. It may be noted that identification module 220 may process the original image 201 received as input or image 201A after being processed by image processing module 110a. Identification module 220 may detect color tags 410 and 420 in sub-image 201B and may determine if the tags are within a predetermined distance range from each other. The identification module 220 may then determine the color of each tag (e.g. the color of tag 410 is identified as pink and color tag 420 is identified as blue). Once the colors on the color tags have been determined, the pig can be identified.

In some embodiments, the color code is dependent on the location of a first color (or grey scale) tag in relation to the second color (or grey scale) tag. Alternatively or in addition, the color code may be dependent on the shapes of the different color (or grey scale) tags.

An alternative color mark identification flow may be implemented using trained neural networks or other machine learning techniques to identify the color tags in the image and to identify the pigs based on the color codes and possibly based on the shape of the pig.

Identification module 220 may use a sequence of images to track the animals to improve the accuracy of their identification. As each animal may move in the pen, image 201 may not capture the entire color marking of the pig in each image, and therefore identification module 220 may fail to identify the animal in some of the images. When a sequence of images is provided to identification module 220, the probability of capturing the entire color marking in at least one of the provided images rises, and the identity of an animal acquired in one image of the sequence may be used in other images of the sequence, in which the animal was tracked and for which the identification failed.

Identification module 220 may use any other suitable techniques to identify the animals. An alternative image processing identification mechanism, used by identification module 220, may be based on tattoos, barcodes, quick response (QR) code or any other uniquely identifiable visible mark located on the upper part of the animal's body, which is visible to imaging device 118. The identification of an individual animal may also be assisted by sensors, other than an image sensor, e.g., including one or more of an and RFID sensor (to identify electronic collars and/or electronic ear tags (e.g. RFID tags)), or a sensor to identify non-electronic collars, non-electronic ear tags and the like.

Figure 5:
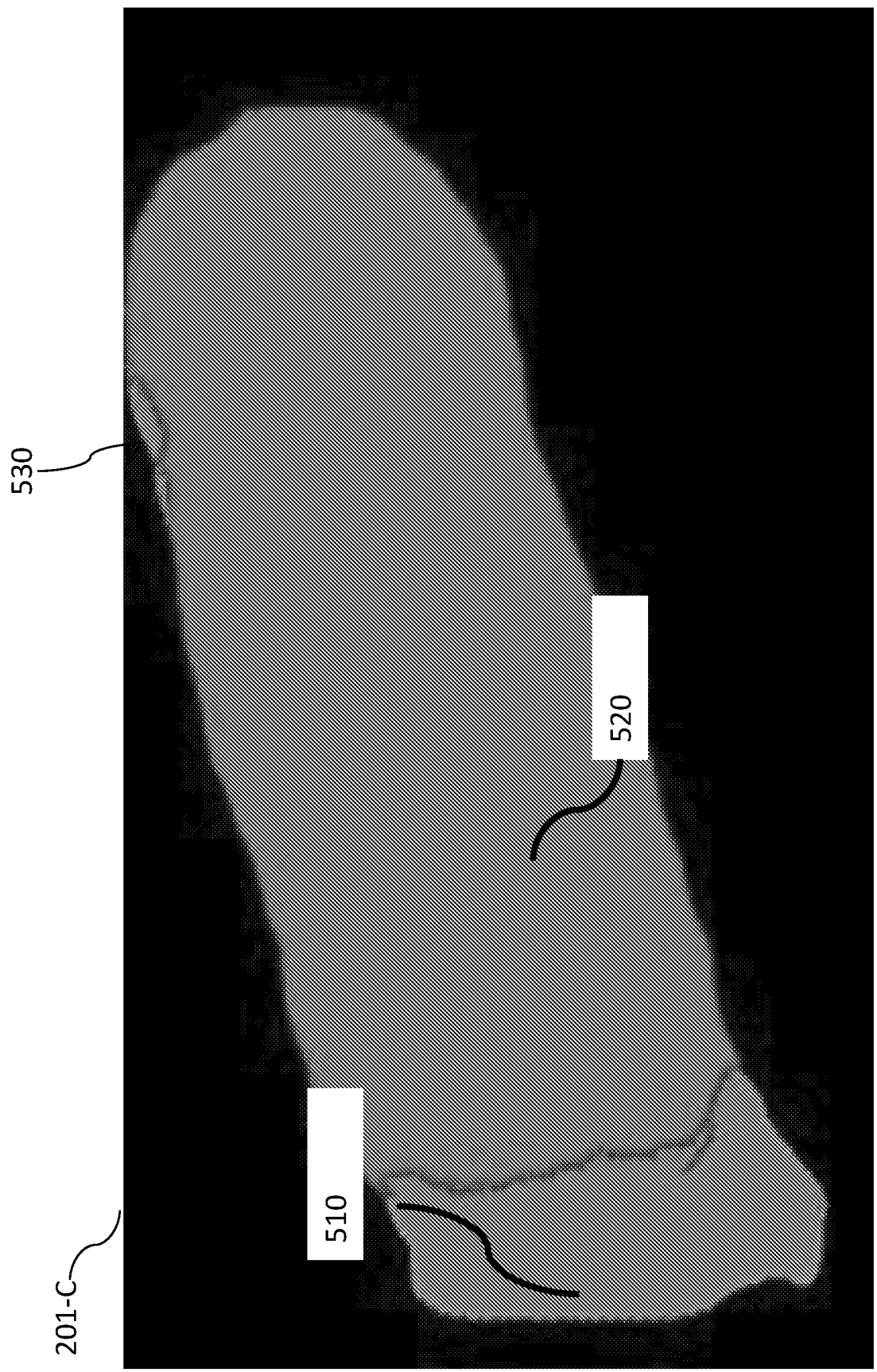
FIG. 5 is an example of an outcome image created by an assessment module, according to embodiments of the invention.

FIG. 5, to which reference is now made, is an example of an outcome image 201C created by assessment module 230 operating on image 201B (FIG. 4B). It may be noted that the same procedure may be implemented on all animals in bounding boxes selected by image processing module 110a. As can be seen in FIG. 5, assessment module 230 may partition or separate the shape in image 201C to three parts representing the head 510, the body 520 and the legs 530.

In one embodiment identification module 220 may operate after assessment module 230 separated the specific animal to a head part and a body part. In this case, identification module 220 may identify the specific animal based on the head part (e.g., based on color tags attached to the animal's ear, as discussed above) and assessment module 230 may assess the physical state of the specific animal based on the body part.

Assessment module 230 may assess the health physical state of an animal from its behavior and locations over time as captured by the images. For example, if an animal does not change its posture and/or location in a predetermined number of consecutive images, assessment module 230 may assess that the animal is sick or dead. If an animal is not detected near the feeding or the water equipment in the pen, in a predetermined number of consecutive images, assessment module 230 may assess that the animal is not in good health. If the average speed of an animal, as computed from its location in a predetermined number of consecutive images, is higher or lower, compared to the average speed of other animals in the pen or to its own speed in the past (e.g., as known from information stored in database 110), assessment module 230 may assess that the animal is sick.

In one embodiment, assessment module 230 may utilize machine learning technics for video content analytics to assess an animal's physical state, e.g., that an animal is giving birth or that an animal is being aggressive and the like. In some embodiments, if an animal is determined to be giving birth for a period longer than a predetermined time and/or if a time between birth of pups is determined to be longer than a predetermined time, a signal may be sent to alert a veterinarian of a difficult labor situation.

Assessment module 230 may assess physical states of the pen, e.g., that some equipment in the pen is malfunctioning when many animals appears to gather near that equipment in a predetermined number of consecutive images. In one embodiment the location of the equipment may be known (predetermined). In another embodiment the equipment is detected automatically, e.g., by processor 13, using objects recognition techniques.

Assessment module 230 may identify physical states related to a single animal such as an animal being pregnant or giving birth; animal is sneezing and/or coughing and/or vomiting and/or losing weight and the like by comparing the animal's location (and possibly its' shape) in consecutive images.

When a plurality of sensors are installed in the pen, assessment module 230 may take into consideration the information collected by the sensors during the assessment process. Assessment module 230 may determine, from the image of the pen, a location of a specific animal and may provide an assessment of the animal's physical state based on its location in the pen combined with the information received from one or more sensors.

The additional information collected by the sensors may be, for example, temperature, noise, humidity and the like. The combination of the input received from the sensors with the image captured by imaging device 118 may improve the quality of the assessment. For example, a directional microphone indicating that an animal is coughing and the location of the coughing animal, a temperature sensor indicating a high temperature in a specific location in the pen, and detection and/or identification of an animal, from the image, at the same location where the high temperature and coughing noise were detected, may increase the likelihood that an animal, possibly, an identified animal, is sick.

In some embodiments, a control module operatively connected to system 100 may react to specific physical states assessed by assessment module 230. For example, the control module may trigger ventilation equipment in the pen to change the ventilation in the pen according to the estimated total weight of the pigs; or trigger the feeding equipment to change the food mixture/quantity to match the weight of the specific pig that approaches the food feeder and the like. In one embodiment, the control module may trigger a painting equipment to mark a pig who's weight approximately reached a pre-defined weight, or who is suspected of being sick. For example, a pig detected in an image and determined to be in a physical state that requires being marked by paint, may be tracked throughout images of the pen to different locations in the pen. Once the location of the pig is determined to be proximate the painting equipment, the control module may send a signal to trigger the painting equipment. The signal may include information such as the location of the pig, the pose of the pig, the pig's speed, etc. to assist in accurately painting the pig.

Figure 6:
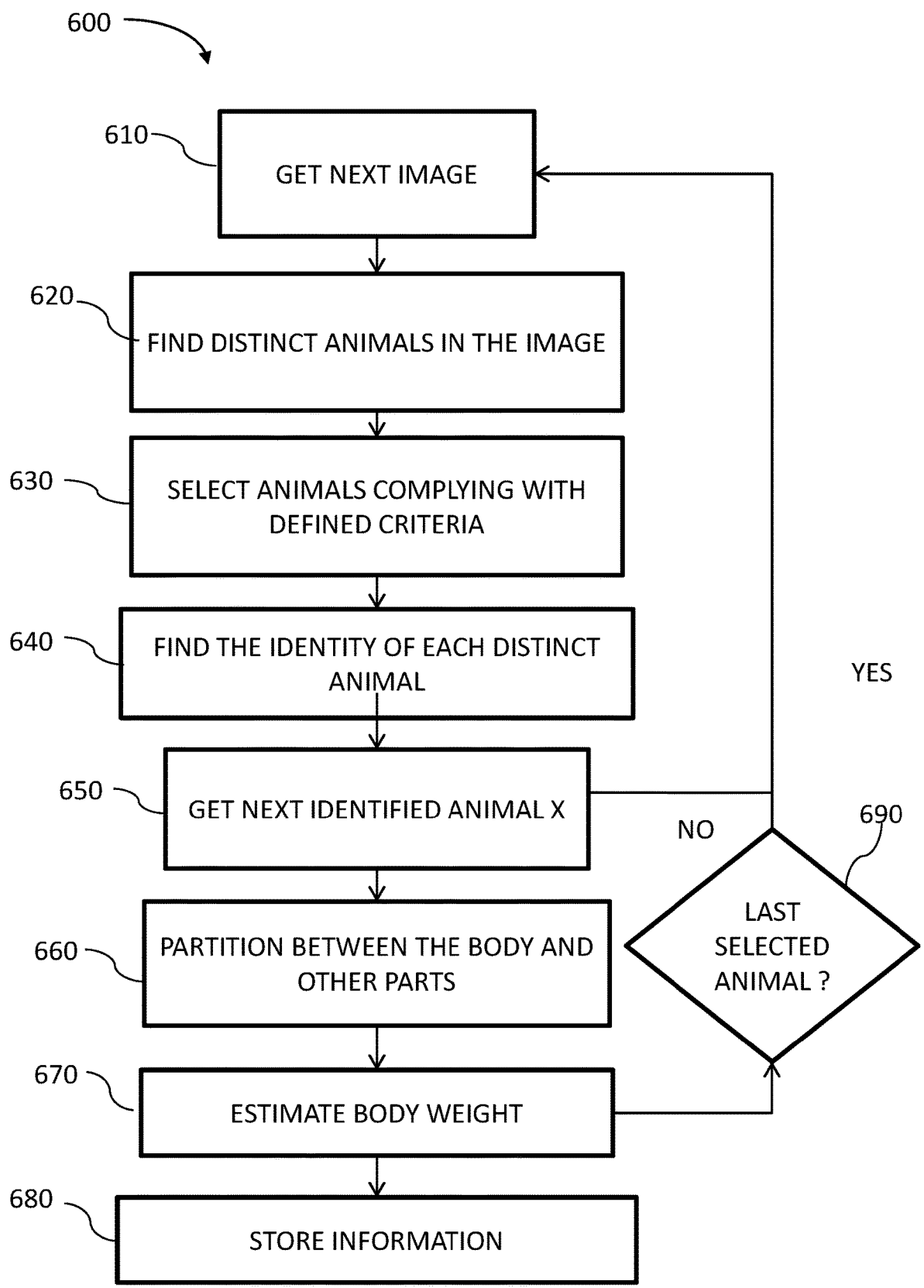
FIG. 6 exemplifies a process run by a monitoring module, according to embodiments of the invention.

FIG. 6, to which reference is now made, is an example of flow 600 implemented by monitoring process 200, constructed and operative in accordance with an embodiment of the present invention. In step 610, monitoring process 200 may receive a new image (e.g. from camera 15). In step 620, image processing module 110a may detect distinct animals in the image. In step 630 image processing module 110a may select only part of the animals (that comply with specific criteria as described in details herein above). In step 640 identification module 220 may identify the distinct animals, e.g. based on color coding, as described above. In step 660 assessment module 230 may partition the animal to its parts and in step 670 assessment module 230 may assess the weight of the body part of the animal. In step 680 control module 240 may store the assessed weight locally or on database 110 in the cloud while in step 690 assessment module 230 may check if there are additional animals to process in the image and if so, may continue with the processing of the next animal (step 650). If there are no more animals to process in the image, the flow may return to step 610 and start processing another image.

In one embodiment, when a color mark is located on the ear of the pig and the physical state to be assessed is the pig's weight the identity of the specific animal may be based on the head part of the animal and the physical state may be assessed based on the body part of that animal.

It may be appreciated by the skilled person that the steps shown in the various flows are not intended to be limiting and that each flow may be practiced with variations.

As mentioned herein above, assessment module 230 may use information calculated and stored in database 110 in the cloud. This information may include images, image related vectors, weight, posture, location, identification and other parameters related to an animal or to plurality of animal or to the entire pen. The information may be extracted from formerly obtained images in the short term (e.g., minutes or hours) and/or long term (e.g., days).

As described herein above, system 100 may be used to monitor a plurality of physical states and to send a plurality of control signals to a plurality of devices in order to perform actions. For example, system 100 may track a physical state (e.g., weight) of an individual animal in the farm and when an animal reaches a predefined physical state (e.g., predefined weight), a predefined action may be triggered. The physical state may be a configured intermediate weight for which the action may be to update food recipes or the physical state may be a configured final weight and the action may be to paint the animal so it can be easily identified.

The physical states monitored by system 100 may be an irregular activity in the pen such as animals gathering near a water supply, animal giving birth, animal coughing and the like for which the action may be to create an appropriate alert and send it to predefined destinations such as the farmer and the veterinarian via a messaging system such as email, SMS and the like.

The physical state may also be related to a facility in the pen and assessment of the physical states, e.g., based on indications received from sensors, such as high temperature and the like, may trigger an action such as starting/increasing/stopping/decreasing ventilation, heating and the like.

In one embodiment the imaging device 118 may be a video camera, which provides series of consecutive images, enabling system 100 to track specific animals over time in order to improve the identification of an animal or the animal's or pen's physical state assessment. As described herein above, color, grey level, or other visible marks may not be clearly visible in each image, the weight assessment may vary between images, health assessment may change and the like, such that using a plurality of images may improve the identification of an animal or the animal's or pen's physical state assessment. In addition, some animal's or pen's physical states may be assessed better when taking into consideration a plurality of images. For example, while assessing the health of an animal, the number of arrivals to the feeding location and the animal's movement during the day and during the night may provide relevant indications of health physical state. Additional examples of physical states that can be identified when using a plurality of images may be persistent aggressive behavior of specific animals; birth giving and the like that can be identified, for example, by video content analytics.

System 100 may provide information to a remotely located farmer, and may trigger actions in order to preserve an optimal environment for the livestock thereby to obtain optimal growth. As mentioned herein above, system 100 may assess the physical state of the livestock in the pen and provide a signal to activate some actions. For example, provide indications that the food recipes should be changed according to the actual size of the livestock; provide early detection of diseases, births and deaths; provide early detection of malfunctioning facilities in the pen such as feeding and water machines; provide information needed for choosing the optimum date of shipment according to the actual weight of the animals (thereby minimizing the costs and maximizing the revenue from the pen). System 100 provides these indications while minimizing human interaction to minimize exposure of the livestock to human thereby reduce events of livestock disease and stress.

In addition, system 100 may provide energy saving by, for example, automatically adjusting ventilation to the actual average/total weight of the livestock.

Unless specifically stated otherwise, as apparent from the following discussions, it is appreciated that throughout the specification discussions utilizing terms such as "assessing", "analyzing", "processing," "computing," "calculating," "determining," "detecting", "identifying" or the like, refer to the action and/or processes of a computer or computing system, or similar electronic computing device, that manipulates and/or transforms data represented as physical, such as electronic, quantities within the computing system's registers and/or memories into other data similarly represented as physical quantities within the computing system's memories, registers or other such information storage, transmission or display devices.

Embodiments of the present invention may include apparatus for performing the operations herein. This apparatus may be specially constructed for the desired purposes, or it may comprise a general-purpose computer selectively activated or reconfigured by a computer program stored in the computer. The resultant apparatus when instructed by software may turn the general purpose computer into inventive elements as discussed herein. The instructions may define the inventive device in operation with the computer platform for which it is desired. Such a computer program may be stored in a computer readable storage medium, suitable for storing electronic instructions and capable of being coupled to a computer system bus.

The present invention may be a system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire. Rather, the computer readable storage medium is a non-transient (i.e., not-volatile) medium.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Java, Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general-purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

What is claimed is:

1. A method of estimating weight of one or more livestock animals, the method comprising:
    receiving at least one image depicting a scene comprising one or more livestock animals;
    processing said at least one image to define, for each of one or more depicted animals, a bounding box enveloping a respective depicted animal of said one or more depicted animals;
    evaluating a suitability of each of said one or more depicted animals for further processing, by determining whether the bounding box thereof has a specific shape, said further processing being performed to determine weight of said one or more depicted animals;
    for a specific animal of those of said one or more depicted animals that are evaluated suitable for further processing, segmenting a respective bounding box to determine boundaries of a segment associated with a head part of the specific animal;
    detecting, within the segment associated with the head part, a visible mark, associated with the specific animal, said visible mark comprising a plurality of tags having more than one color and being attached to the specific animal;
    assigning an identification to the specific animal according to a color code configuration pre-defined based on a combination of colors of said plurality of tags, provided that two colors of said more than one color are detected within a predetermined distance range from each other; and
    further processing said at least one image to determine weight of the specific animal.

2. The method of claim 1, wherein said scene comprises a livestock group housing environment.

3. The method of claim 1, wherein said at least one image is captured from an overhead perspective in relation to said one or more livestock animals.

4. The method of claim 3, wherein, said evaluating the suitability is further made based on a predetermined set of parameters with respect to each of said one or more depicted animals, said set of parameters comprising at least one of: an angle of said overhead perspective in relation to a bounding box in said at least one image, a location of a bounding box in said at least one image relative to an acquisition point of said at least one image, visibility of said one or more depicted animals in said scene, location of said one or more depicted animals in said scene, occlusion of said one or more animals in said scene, and a bodily posture of said one or more depicted animals in said scene.

5. The method of claim 1, wherein said evaluating the suitability comprises assigning a suitability score to the bounding box of each of the one or more depicted animals, and wherein the one or more depicted animals are evaluated suitable for further processing when said suitability score assigned to the bounding box exceeds a specified threshold.

6. The method of claim 1, wherein said processing of said at least one image to define, for each of said one or more depicted animals, the bounding box comprises applying a machine learning detection algorithm, said machine learning detection algorithm being trained to: (i) classify images to ones depicting animals and ones not depicting animals; and (ii) in the images depicting animals, separate between depicted animals by creating the bounding box around each depicted animal in said images.

7. The method of claim 1, wherein said further processing comprises for each of the depicted animals suitable for the further processing: segmenting a respective bounding box to determine boundaries of a segment associated with a bodily trunk of a respective depicted animal; and determining weight of the respective depicted animal, based on said boundaries of the segment associated with said bodily trunk.

8. The method of claim 7, wherein said determining of said boundaries of the segment associated with said bodily trunk of said respective depicted animal comprises applying a trained machine learning segmentation algorithm, and wherein said machine learning segmentation algorithm is trained using a training set comprising:
(i) a plurality of images of livestock animals, wherein said images are captured from an overhead perspective; and
(ii) labels associated with boundaries of segments of at least some of a bodily trunk, a head, a tail, and one or more limbs of each of said animals in said plurality of images.

9. The method of claim 7, wherein said determining weight of the respective depicted animal comprises:
based on the respective bounding box, extracting image information comprising coordinates of pixels in the image, distance of pixels of the segment from the middle of the image, number of pixels in the segment, and a center of gravity of the respective depicted animal in the image;
using, as input to a respectively trained machine learning algorithm, a vector comprising said image information, to determine weight of the respective depicted animal.

10. The method of claim 7, further comprising:
(i) receiving a sequence of images of said scene, (ii) tracking at least one of said one or more depicted animals in said sequence of images, (iii) determining an identity of said at least one animal, based on at least one image in said sequence of images, and (iv) assigning said identity to said at least one animal in all images in said sequence of images;
wherein said tracking is based on at least one of (a) the defined bounding box, (b) the boundaries of the segment associated with the bodily trunk, or (c) the boundaries of the segment associated with the head part.

11. The method of claim 1, wherein said one or more tags are attached to an ear of the specific animal.

12. The method of claim 1, wherein tags of said plurality of tags have different greyscale level and/or different shape, further defining the color code configuration.

13. The method of claim 1,
further comprising declaring unsuccessful identification when said two colors are detected beyond the predetermined distance range from each other or when more than two colors of said more than one color are detected within the predetermined distance range.

14. A system for estimating weight of one or more livestock animals, the system comprising:
at least one hardware processor; and
a non-transitory computer-readable storage medium having stored thereon program instructions, the program instructions executable by the at least one hardware processor to:
receive at least one image depicting a scene comprising one or more livestock animals,
define, for each of one or more depicted animals, a bounding box enveloping a respective depicted animal of said one or more depicted animals,
evaluate a suitability of each of said one or more depicted animals for further processing, by determining whether the bounding box thereof has a specific shape, said further processing being performed to determine weight of said one or more depicted animals,
for a specific animal of those of said one or more depicted animals that are evaluated suitable for further processing, segment a respective bounding box to determine boundaries of a segment associated with a head part of the specific animal;
detect, within the segment associated with the head part, a visible mark, associated with the specific animal, said visible mark comprising a plurality of tags having more than one color and being attached to the specific animal;
assign an identification to the specific animal according to a color code configuration pre-defined based on a combination of colors of said plurality of tags, provided that two colors of said more than one color are detected within a predetermined distance range from each other; and
further process the image to determine weight of the specific animal.

15. A computer program product comprising a non-transitory computer-readable storage medium having program instructions embodied therewith, the program instructions executable by at least one hardware processor to:
receive at least one image depicting a scene comprising one or more livestock animals;
define, for each of one or more depicted animals, a bounding box enveloping a respective depicted animal of said one or more depicted animals;
evaluate a suitability of each of said one or more depicted animals for further processing, by determining whether the bounding box thereof has a specific shape, said further processing being performed to determine weight of said one or more depicted animals;
for a specific animal of those of said one or more depicted animals that are evaluated suitable for further processing, segment a respective bounding box to determine boundaries of a segment associated with a head part of the specific animal;
detect, within the segment associated with the head part, a visible mark, associated with the specific animal, said visible mark comprising a plurality of tags having more than one color and being attached to the specific animal;
assign an identification to the specific animal according to a color code configuration pre-defined based on a combination of colors of said plurality of tags, provided that two colors of said more than one color are detected within a predetermined distance range from each other; and
further process the image to determine weight of those of said one or more depicted animals that are evaluated suitable for further processing the specific animal.

* * * * *